(12) United States Patent
Ehrenfeld

(10) Patent No.: US 6,956,140 B2
(45) Date of Patent: Oct. 18, 2005

(54) HYDROTHERMAL HYDROLYSIS OF HALOGENATED COMPOUNDS

(75) Inventor: Robert L. Ehrenfeld, New York, NY (US)

(73) Assignee: Halocarbon Products Corporation, River Edge, NJ (US)

( * ) Notice: Subject to any disclaimer, the term of this patent is extended or adjusted under 35 U.S.C. 154(b) by 316 days.

(21) Appl. No.: 10/149,690

(22) PCT Filed: Dec. 13, 2000

(86) PCT No.: PCT/US00/33701

§ 371 (c)(1),
(2), (4) Date: Jan. 31, 2003

(87) PCT Pub. No.: WO01/44149

PCT Pub. Date: Jun. 21, 2001

(65) Prior Publication Data

US 2004/0110993 A1 Jun. 10, 2004

Related U.S. Application Data

(60) Provisional application No. 60/170,618, filed on Dec. 14, 1999.

(51) Int. Cl.$^7$ ................ C07C 31/38; C07C 31/34; C07C 31/40; C07C 31/42
(52) U.S. Cl. ................ 568/842; 568/840; 568/841
(58) Field of Search .................. 568/842, 840, 568/841

(56) References Cited

U.S. PATENT DOCUMENTS 4,590,310 A * 5/1986 Townsend et al. .......... 568/842

* cited by examiner

Primary Examiner—Elvis O. Price
(74) Attorney, Agent, or Firm—Norris McLaughlin & Marcus PA

(57) ABSTRACT

A process for preparing a halogenated alcohol comprising hydrolyzing a halogenated precursor of the halogenated alcohol in water at a temperature near but below the critical point of water. For example, the halogenated alcohol has the formula $CF_3(CF_2)_nCH_2OH$, wherein n is zero or a whole number from 1 to 5, the halogenated precursor has the formula $CF_3(CF_2)_nCH_2Cl$, wherein n is as defined above, and the process comprises hydrolyzing the halogenated precursor in water at a temperature near but below the critical point of water. In a particularly preferred embodiment, the halogenated alcohol has the formula $CF_3CH_2OH$, the halogenated precursor has the formula $CF_3CH_2Cl$, and the process comprises hydrolyzing $CF_3CH_2Cl$ in water at a temperature near but below the critical point of water.

5 Claims, 2 Drawing Sheets

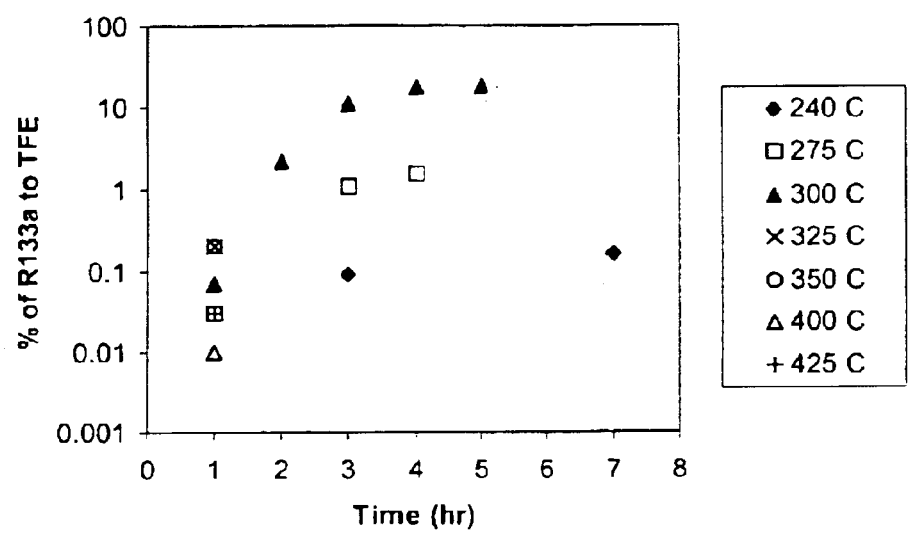
Figure 1: Percent of R133a converted to TFE in batch bomb reactor.

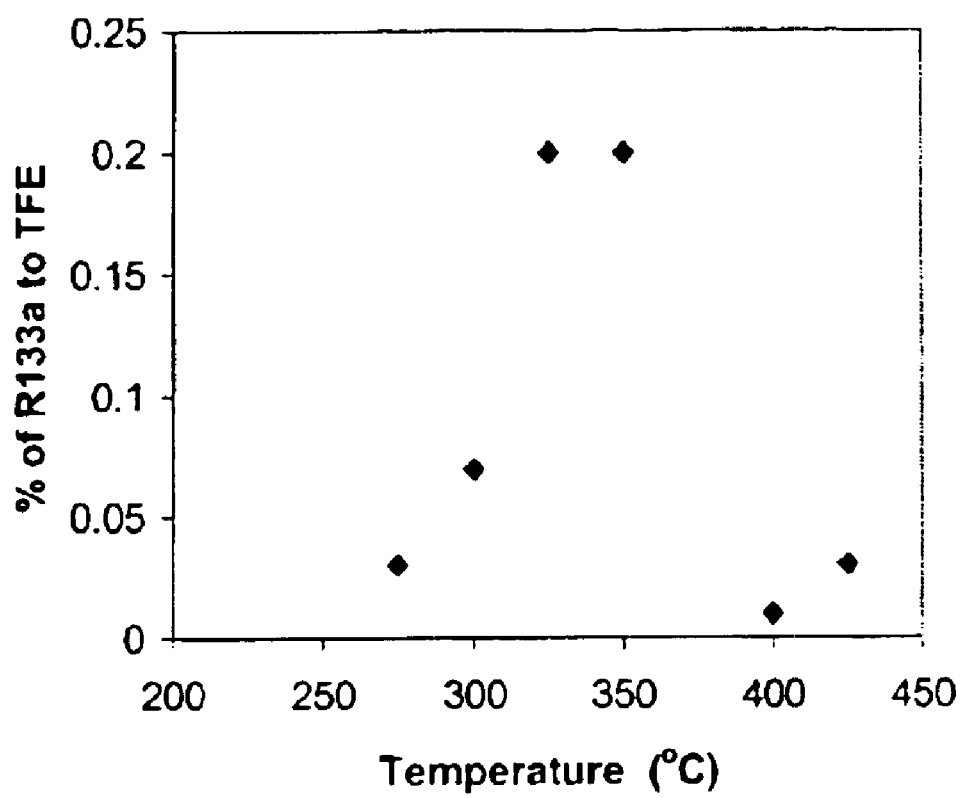
Figure 2: Percent of R133a converted to TFE after 1 hour in batch bomb reactor.

HYDROTHERMAL HYDROLYSIS OF HALOGENATED COMPOUNDS

This application claims benefit of provisional application 60/170,618 filed Dec. 14, 1999.

BACKGROUND OF THE INVENTION

1. Field of the Invention

The present invention relates to process for preparing halogenated alcohols.

2. Description of Related Art

Currently most fluorinated alcohols and fluorinated organic acids are manufactured in processes that depend heavily on large quantities of halogenated solvents. The proper handling and disposing of these solvents cause serious problems and costs for the industries that use them.

SUMMARY OF THE INVENTION

The object of the present invention was to develop a process for preparing halogenated alcohols that would not utilize halogenated solvents.

These and other objects were met by the present invention, which relates to a process for preparing a halogenated alcohol comprising hydrolyzing a halogenated precursor of said halogenated alcohol in water at a temperature near but below the critical point of water.

BRIEF DESCRIPTION OF THE DRAWINGS

The invention will now be described in greater detail with reference to the drawings, wherein:

FIG. 1 is a graph showing the percentage of 1,1,1-trifluoro-2-chloroethane [R133a] converted to trifluoroethanol [TFE] in a batch bomb reactor using the inventive process; and FIG. 2 is a second graph showing the percentage of 1,1,1-trifluoro-2-chloroethane [R133a] converted to trifluoroethanol [TFE] in a batch bomb reactor using the inventive process, but this time after 1 hour elapsed time.

DETAILED DESCRIPTION OF THE INVENTION

The inventive process provides a safer and less costly process for preparing halogenated alcohols from the halogenated precursors thereof. The inventive process involves hydrolysis, i.e., the rupture of chemical bonds by the addition of water. Accordingly, the phrase "halogenated precursor of said halogenated alcohol" is meant to embrace any halogenated compound that contains a functional group that can be converted to a hydroxyl group upon reaction with water to thereby yield a halogenated alcohol.

In a preferred embodiment, the inventive process is used to make halogenated alcohol compounds of the formula $CF_3(CF_2)_nCH_2OH$, wherein n is zero or a whole number from 1 to 5. In this embodiment, the halogenated precursor has the formula $CF_3(CF_2)_nCH_2Cl$, wherein n is as defined above, and the process comprises hydrolyzing said halogenated precursor in water at a temperature near but below the critical point of water.

In an especially preferred embodiment, the inventive process is used to make trifluoroethanol [TFE], which has the formula $CF_3CH_2OH$. In this embodiment, the halogenated precursor is 1,1,1-trifluoro-2-chloroethane [R133a], which has the formula $CF_3CH_2Cl$, and the process comprises hydrolyzing R133a in water at a temperature near but below the critical point of water.

The critical point of water is 374° C. and 221 bar. The phrase "at a temperature near but below the critical point of water" means that the temperature of the water during the reaction should be maintained near but below 374° C. By "near" is meant within 100° C. of the critical temperature. In the especially preferred embodiment, wherein R133a is hydrolyzed, the temperature is maintained from 275 to 325° C. at subcritical pressure.

The time of the reaction is a result-effective-parameter, and persons skilled in the art will be able to optimize the yield of the halogenated alcohol by varying the reaction time. In the especially preferred embodiment, wherein R133a is hydrolyzed to TFE, the reaction time is maintained from 3 to 5 hours.

The invention will now be described in even greater detail with reference to the following example.

EXAMPLE

Exploratory hydrolysis of 1,1,1-trifluoro-2-chloroethane [R133a] to trifluoroethanol [TFE], ($CF_3CH_2Cl + H_2O \rightarrow CF_3CH_2OH + HCl$) was performed in subcritical and supercritical water. The experimental reactor and procedures used are discussed below.

Reactors. Batch bomb reactors were constructed of 316 stainless steel and had an outside diameter of 0.75 inch and an inside diameter of 0.51 inch (wall thickness was 0.12 inch). Typical reactors were 7.5 inches long providing an internal volume of 26.2 mL once fittings were attached. The internal volume of each reactor was measured by filling with water. One end of the reactor was plugged. The other end had a reducing union connected to $1/16$ inch tubing (approximately 3 feet) that was attached to a valve. The valve allowed for the purging of the unpressurized system with nitrogen, feeding of gaseous reactants into the reactor, and collection of the reactor contents. No direct temperature or pressure measurements were made on the reactor.

Once the reactor was sealed it was placed in an isothermal sand bath. The time required for heating the reactor (with only water in it) was previously measured with a thermocouple in place of the end plug for various sand bath temperatures. The heat up time was always significantly less (<5 min for the highest temperatures) than the reaction times (>30 mins). Therefore, the reaction temperature was assumed to be the temperature of the sand bath.

The pressure of the system was calculated using the temperature, amount of water, volume of the reactor, and steam tables. Because the system is dilute in reactants, the pure water data used to calculate the pressure is sufficiently accurate.

To quench the reaction, the bomb reactor was removed from the sand bath and placed in an ice water bath. The reactor contents were then analyzed. Typical reaction times were from 30 minutes to 7 hours.

Feed and Collection Procedure. R133a has a normal boiling temperature of 6.1° C. Therefore, it was stored as a saturated vapor-liquid mixture in a sealed lecture bottle without a regulator adapter at a pressure of 25 psi (1.724 bar) and was delivered in the gas phase into the bomb reactors.

The bomb reactors were disassembled and then washed with water and dried in the atmosphere at 150° C. for 4 hours. After cooling of the reactor, the bottom plug was placed on the reactor and a fixed amount of water added. The top $1/16$ inch tubing and valve assembly was then attached. The system was purged with nitrogen for 10 minutes. A direct connection to the lecture bottle was made to deliver gas to the bomb reactors. The reactor was flushed twice with R133a before the final addition of the reactant. The amount of R133a added to the system was calculated from the available headspace in the reactor, the temperature, and pressure using the ideal gas law, neglecting solubility of R133a in water. Similar drying and purging procedures were followed when a liquid reactant was used.

After cooling, the bomb reactors would return to their initial pressure (roughly atmospheric). The bomb reactors would be opened and the liquid analyzed. To determine the unreacted R133a in the system the bomb reactor was cooled to 0–3° C. and 8 ml of cold (−15° C.) tetrachloroethylene was injected into the reactor and shaken. The reactor was sealed and placed in the freezer for 5–10 minutes. The reactor was then opened and both the water and organic phases were analyzed for the starting material and desired product. The samples were kept close to 0° C. Only the water phase was analyzed for free Cl⁻ and F⁻. Control recovery experiments (i.e. reactors loaded with water and R133a without being heated) were performed and 90±5% of the R133a was recovered.

Analytical Techniques. Aqueous and organic samples were analyzed by GC FID. R133a, TFE, and trifluoroacetic acid were quantitatively measured. Aqueous samples were also analyzed for free chloride and free fluoride. Free chloride was measured by two methods, a chloride specific electrode and a colorometric adsorption method (mercuric thiocyanate reacts with chloride ion to produce thiocyanate ion that is then reacted with ferric ammonium sulfate to form red ferric thiocyanate that adsorbs at 463 nm). Free fluoride was measured with the SPADNS colorometric adsorption method (fluoride ion reacts with a zirconium-dye lake, dissociating a portion of it to the colorless anion $ZrF_6^{-2}$ thus decreasing the adsorption at 570 nm).

Results. In the first set of experiments only the liquid phase was collected and analyzed. Water fed into the reactor was in the range of 2 to 8 mL (111 to 444 mmol) while R133a fed to the reactor was always significantly less (1.3 to 1.7 mmol) because it was delivered in the gas phase. The amount of water added to the system was chosen to prevent total vaporization of the water at the desired reaction temperature thus not allowing the pressure to exceed safety limits for this closed batch reactor. Reaction times were from 30 minutes to 7 hours. Temperatures explored were 240 to 425° C. Pressures were always calculated from the saturation point of pure water given the volume of the reactor and the temperature.

Table 1 contains the results for the hydrolysis of R133a in batch reactors when only the liquid phase was collected and analyzed. If R133a reacts only through hydrolysis to TFE and HCl and the TFE does not react further, then the amount of free chloride would be equal to the amount of TFE formed (on a mole basis). However, the measured Cl⁻ concentration was always higher. In addition, some fluoride was found showing that some other reactions are also occurring.

FIGS. 1 and 2 use the data presented in Table 1 to show how temperature and reaction time affect the conversion of R133a to TFE. The conversion to byproducts is not accounted for in these figures.

TABLE 1

Hydrolysis of R133a, liquid phase analysis.

| Temperature (° C.) | Pressure (bar) | Time (hr) | $H_2O$ (mmole) | Initial R133a (mmole) | R133a to TFE (mole %) |
|---|---|---|---|---|---|
| 240 | 34 | 3 | 444 | 1.27 | 0.09 |
| 240 | 34 | 7 | 444 | 1.27 | 0.16 |
| 275 | 60 | 1 | 444 | 1.27 | 0.03 |
| 275 | 60 | 3 | 444 | 1.27 | 1.11 |
| 275 | 60 | 4 | 444 | 1.27 | 1.56 |
| 300 | 86 | 1 | 444 | 1.27 | 0.07 |
| 300 | 86 | 2 | 444 | 1.27 | 2.20 |
| 300 | 86 | 3 | 444 | 1.27 | 11.21 |
| 300 | 86 | 3 | 444 | 1.27 | 10.87 |
| 300 | 86 | 4 | 444 | 1.27 | 17.55 |
| 300 | 86 | 5 | 444 | 1.27 | 18.49 |
| 325 | 121 | 1 | 444 | 1.27 | 0.20 |
| 350 | 165 | 1 | 222 | 1.54 | 0.20 |
| 400 | 185 | 1 | 111 | 1.68 | 0.01 |
| 425 | 227 | 1 | 111 | 1.68 | 0.03 |

Note:
The critical point of water is 374° C. and 221 bar. To be "supercritical," both the temperature and pressure must be above this point. The last entry in Table 1 is supercritical, while the second to last entry is only supercritical with respect to the temperature. All other entries are subcritical.

Table 2 displays the results obtained from running batch bomb reactor experiments in which R133a was recovered using the extraction into cold tetrachloroethylene method as described in the experimental section. In all experiments 444 mmol of water and 1.27 mmol of R133a were charged to the reactor. The percent of R133a recovered and converted to TFE is reported. The theoretical yield based on the R133a consumed is also given.

Conclusions. Yields of TFE in the vicinity of 10% can be made at 275° C., but yields as high as 26% were made at 300° C. At 325° C. and higher temperatures, yields were lower even at shorter times of exposure. The yields were quite low above the critical point of water.

No attempt was made to optimize the reaction conditions, but it is obvious that the hydrolysis of this type of halogenated compound, while inert to water at the usual reaction conditions, can be effected by using temperatures in the vicinity of the critical point of water, but not exceeding it.

It will also be apparent to persons skilled in the art that the foregoing discovery is applicable to higher homologs of R133a and other halogenated compounds as well.

TABLE 2

Hydrolysis of R133a, liquid and extraction of vapor phase analysis.

| Temp (° C.) | Press. (bar) | Time (hr) | R133a to TFE (mole %) | TFE Made (mmole) | R133a Recovered (%) | R133a Consumed (mmoles) | TFE Yield (mole %) |
|---|---|---|---|---|---|---|---|
| 275 | 60 | 1 | 0.03 | 0.00 | 10.18 | 1.14 | 0.03 |
| 275 | 60 | 3 | 1.12 | 0.01 | 11.09 | 1.13 | 1.26 |
| 275 | 60 | 3 | 1.02 | 0.01 | 89.42[a] | 0.13 | 9.64 |
| 300 | 86 | 2 | 2.20 | 0.03 | 9.98 | 1.14 | 2.44 |
| 300 | 86 | 2 | 2.80 | 0.04 | 69.47[a] | 0.39 | 9.17 |
| 300 | 86 | 2 | 4.49 | 0.06 | 59.93[a] | 0.51 | 11.21 |
| 300 | 86 | 3 | 11.21 | 0.14 | 11.82 | 1.12 | 12.71 |
| 300 | 86 | 3 | 10.87 | 0.14 | 9.61 | 1.15 | 12.03 |
| 300 | 86 | 3 | 11.79 | 0.15 | 54.81[a] | 0.57 | 26.09 |
| 300 | 86 | 3 | 9.54 | 0.12 | 58.27[a] | 0.53 | 22.86 |
| 300 | 86 | 4 | 17.55 | 0.22 | 12.37 | 1.11 | 20.03 |
| 300 | 86 | 4 | 15.52 | 0.20 | 31.66[a] | 0.87 | 22.71 |
| 300 | 86 | 5 | 17.55 | 0.22 | 9.6 | 1.15 | 19.41 |
| 300 | 86 | 5 | 15.52 | 0.20 | 23.94 | 0.97 | 20.40 |
| 325 | 121 | 1 | 0.20 | 0.00 | 16.72 | 1.06 | 0.24 |
| 325 | 121 | 2 | 1.02 | 0.01 | 40.97[a] | 0.75 | 1.73 |
| 325 | 121 | 3 | 1.10 | 0.01 | 6.83 | 1.18 | 1.18 |

[a]These entries used the cold tetrachloroethylene extraction technique.
Note:
For all of the conditions, 444 mmol of water and 1.27 mmol of R133a were initially placed in the reactor.

It will further be appreciated that the instant specification and claims are set forth by way of illustration and not limitations and that various modifications and changes may be made without departing from the spirit and scope of the present invention.

What is claimed is:

1. A process for preparing a halogenated alcohol comprising hydrolyzing a halogenated precursor of said halogenated alcohol in water in the absence of a carboxylic acid salt at a temperature near but below the critical point of water.

2. The process according to claim 1, wherein the halogenated alcohol has the formula $CF_3(CF_2)_nCH_2OH$, wherein n is zero or a whole number from 1 to 5, the halogenated precursor has the formula $CF_3(CF_2)_nCH_2Cl$, wherein n is as defined above, and the process comprises hydrolyzing said halogenated precursor in water in the absence of a carboxylic acid salt at a temperature near but below the critical point of water.

3. The process according to claim 2, wherein the halogenated alcohol has the formula $CF_3CH_2OH$, the halogenated precursor has the formula $CF_3CH_2Cl$, and the process comprises hydrolyzing $CF_3CH_2Cl$ in water in the absence of a carboxylic acid salt at a temperature near but below the critical point of water.

4. The process according to claim 1, which comprises hydrolyzing $CF_3CH_2Cl$ in water in the absence of a carboxylic acid salt at a temperature between 275° C. to 325° C. at subcritical pressure.

5. The process according to claim 4, wherein said hydrolyzing is carried out for a period of 3–5 hours.

* * * * *